(12) United States Patent
Fedinec (10) Patent No.: US 9,084,598 B2
(45) Date of Patent: Jul. 21, 2015

(54) SUTURE TREATMENT METHOD AND SUTURE CONSTRUCTION/KIT THEREFOR

(76) Inventor: James J. Fedinec, Darien, IL (US)

(*) Notice: Subject to any disclaimer, the term of this patent is extended or adjusted under 35 U.S.C. 154(b) by 655 days.

(21) Appl. No.: 13/506,720

(22) Filed: May 11, 2012

(65) Prior Publication Data

US 2012/0232589 A1 Sep. 13, 2012

Related U.S. Application Data

(63) Continuation-in-part of application No. 12/380,222, filed on Feb. 25, 2009, now abandoned.

(51) Int. Cl.
*A61B 17/04* (2006.01)
*A61B 17/06* (2006.01)
*A61B 19/00* (2006.01)

(52) U.S. Cl.
CPC ....... *A61B 17/06166* (2013.01); *A61B 17/0466* (2013.01); *A61B 2019/444* (2013.01)

(58) Field of Classification Search
CPC .............. A61B 17/0466; A61B 17/06166; A61B 2019/444
USPC .......... 606/228–231, 139, 144, 148; 206/438, 206/441, 63.1; 128/898; 428/364
See application file for complete search history.

(56) References Cited

U.S. PATENT DOCUMENTS

| | | | |
|---|---|---|---|
| 1,382,715 A | 6/1921 | Davis | |
| 1,982,304 A * | 11/1934 | Holden | 428/364 |
| 3,762,418 A | 10/1973 | Wasson | |
| 3,949,755 A | 4/1976 | Vauquois | |
| 4,364,393 A | 12/1982 | Yasnitsky et al. | |
| 6,029,806 A | 2/2000 | Cerwin et al. | |
| 6,610,071 B1 | 8/2003 | Cohn et al. | |
| 6,626,865 B1 | 9/2003 | Prisell | |
| 6,994,719 B2 | 2/2006 | Grafton | |
| 7,029,490 B2 | 4/2006 | Grafton et al. | |
| 2003/0064646 A1 * | 4/2003 | Brown et al. | 428/364 |

* cited by examiner

*Primary Examiner* — Julian W Woo
(74) *Attorney, Agent, or Firm* — Christopher J. Scott (57) ABSTRACT

A suture method, suture construction, and suture kit enables health care providers and patients to select colored sutures from a wide variety of colors. The variously colored sutures enable the patient to adorn a skin wound site so as to more effectively treat the wound with patient input and cooperation. The suturing method involves the steps of assessing a suture site or skin wound; selecting a suturing technique based on the assessed suture site or skin wound; providing a visual depiction of exemplary suture layout schema to the patient, which exemplary suture layout schema are reflective of the selected suturing technique; providing a patient with a selection of suture colors; inviting the patient to select at least one suture color from the suture color palette; selecting at least one suture color from the selection of suture colors; and suturing a suture site with a variously colored suture as selected by the patent.

19 Claims, 10 Drawing Sheets

SUTURE TREATMENT METHOD AND SUTURE CONSTRUCTION/KIT THEREFOR

PRIOR HISTORY

This application is a Continuation-in-Part patent application claiming the benefit of U.S. patent application Ser. No. 12/380,222, filed in the United States Patent and Trademark Office on 25 Feb. 2009 now abandoned, the specifications of which are hereby incorporated by reference thereto.

BACKGROUND OF THE INVENTION

1. Field of the Invention

The present invention generally relates to a method for treating skin wound sites via sutures. More particularly, the present invention relates to a suturing method and/or suture construction and/or suture kit for outfitting or adorning a skin wound site by way of sutures of variously colored/patterned sutures.

2. Description of the Prior Art

A suture is a threadlike medical device that doctors, and especially surgeons, use to hold skin, internal organs, blood vessels and all other tissues of the human body together, after they have been severed by injury or surgery. The threadlike devices typically have relatively high tensile strength; are non-toxic, non-wicking, and hypoallergenic. Further, they typically have a high degree of flexibility and easy to work with so that suture sites may be quickly attended to, and sutures may be quickly knotted.

State of the art, non-absorbable sutures are typically formed from polyethylene or other high strength polymeric materials and come in a limited variety of colors; usually black or blue/violet. When outfitted upon an external suture site, the lack of color variety or the limited black/blue color scheme leaves patients with a visibly unattractive wound and treatment structure. The prior art that addresses colored sutures for wound treatment is limited in scope. Some of the more pertinent art relating to colored suture constructions and/or other means for adorning a skin wound site are briefly described hereinafter.

For example, U.S. Pat. No. 1,382,715 ('715 Patent), which issued to Davis, discloses a Surgical Suture. The surgical suture according to the '715 Patent comprises a coal tar preparation rendering the suture antiseptic and dyeing the same in a variety of colors, including yellow, violet, blue, scarlet, green, orange, and indigo. The colors are provided, in part, so that the user may more readily identify the type of suture by imparting to the suture a particular dye/color.

U.S. Pat. No. 3,762,418 ('418 Patent), which issued to Wasson, discloses a Surgical Suture. The surgical suture according to the '418 Patent is designed for ligating, tying or suturing two sutures simultaneously with a single maneuver. An eyeless needle is swaged to an end of a main suture section. The main suture section ends are fused portions of two separate strands of suture material. The separate strands form an intermediate portion of the main suture section between fused portions. Alternatively, the main suture section may have a plurality of intermediate separate suture strand portions connected to each other by fused portions. Marking bands are located at the junctions of the fused portions with the intermediate separate strand portions.

U.S. Pat. No. 3,949,755 ('755 Patent), which issued to Vauquois, discloses a Surgical Ligature. The surgical ligature according to the '755 Patent is a surgical ligature in which a sterile thread has a surface on which is a succession of areas, for example, lines or dots, of contrasting shades, whereby at least one of the shades appears dark through a film of blood and at least one of the shades appears light through a film of blood. Such a ligature can readily be seen by the surgeon through the blood and against the background of the organ being stitched.

U.S. Pat. No. 4,364,393 ('393 Patent), which issued to Yasnitsky et al., discloses an Absorbable Surgical Suture Material. The absorbable surgical suture material of the '393 Patent is based on monocarboxycellulose. A method for producing said material consists in that cellulose threads are first threaded with nitrogen oxides, then for 0.5 to 2.0 hours treated with a 0.5-2.0-percent solution of a salt of a transition metal with a coordination number not less than 4 in a suitable solvent, and after this treated for 0.5 to 2.0 hours with a 1.0-2.0-percent solution of a polydentate complexing agent in a suitable solvent. Various suture colors are disclosed in the '393 Patent, including sutures of various shades of green, yellow, and gray.

U.S. Pat. No. 6,029,806 ('806 Patent), which issued to Cerwin et al., discloses a Package for Double Armed Sutures. The suture package according to the '806 Patent includes a base panel with a needle park and a plurality of pockets having plural compartments stacked in the Z direction. The package is suitable for containing and dispensing a plurality of double-armed sutures during time-critical surgery and promotes tangle-free dispensing by winding the sutures through the compartments in a serpentine manner to avoid suture-to-suture interaction. Spatial separation of the needles in the needle park and color coding of the sutures allows for easy identification of the individual sutures during dispensing and when tying off the sutures during surgery.

U.S. Pat. No. 6,610,071 ('071 Patent), which issued to Cohn et al., discloses a Suture System. The suture system according to the '071 patent includes a plurality of double-stranded needles connected in sequence with a single-stranded needle at each end. The double-stranded suture needles incorporate two suture strands into a single needle. The suture strands may be of varied coloration to generally aid the user and more particularly to facilitate the implantation of valve prostheses.

U.S. Pat. No. 6,626,865 ('865 Patent), which issued to Prisell, discloses a Method and Device for Marking Surfaces. The method and device according to the '865 patent indicate the periphery line of a patch of an optionally resilient surface layer of a substrate object which patch is intended to be removed in a step, which may cause a change of the appearance of the surface. The method comprises the application on the surface of an adhesive mask, comprising an outer, "negative: and/or optionally an inner, slat "positive" mask component, comprising one or more layers of a sheet material, which can be brought to adhere to the surface of the object.

The negative mask comprises a main opening with a borderline, which forms an inner borderline of the mask, and the positive mask comprises a slab with a borderline, which forms an outer borderline of the mask, said inner and/or outer borderlines having essentially the shape of the intended periphery line of the patch of the surface layer intended to be removed, said main opening of slab having circular or preferably elongated, non-circular shape, preferably with a ratio of lengthwise extension on transverse extension of at least 2 or at least 3 and optionally at most 10.

U.S. Pat. No. 6,994,719 ('719 Patent), which issued to Grafton, discloses a High Strength Suture with Colored Trace at One End. The '719 Patent describes a high strength abrasion resistant surgical suture material with improved tie down characteristics that is color coded for visualization and identification purposes. The suture features a multifilament cover formed of strands of ultra high molecular weight long chain polyethylene braided with polyester, nylon or a bioabsorbable material.

Selected nylon fibers in the cover are provided in a color contrasting with the other cover fibers to provide an identifiable trace. The cover surrounds a core formed of twisted strands of ultrahigh molecular weight polyethylene. The suture, provided in a #2 size, has the strength of #5 Ethibond, is ideally suited for most orthopedic procedures, and can be attached to a suture anchor or a curved needle. The identifiable trace preferably is provided along one half of the length of the suture, so that when the suture is loaded onto a suture anchor, for example, the two legs of the length of suture on either side of the suture anchor can be readily identified.

U.S. Pat. No. 7,029,490 ('490 Patent), which issued to Grafton et al., discloses a High Strength Suture with Coating and Colored Trace. The '490 Patent also describes a high strength abrasion resistant surgical suture material with improved tie down characteristics that is color coded for visualization and identification purposes. The suture features a multifilament cover formed of strands of ultra high molecular weight long chain polyethylene braided with polyester, nylon or a bioabsorbable material.

Selected nylon fibers in the cover are provided in a color contrasting with the other cover fibers to provide an identifiable trace. The cover surrounds a core formed of twisted strands of ultrahigh molecular weight polyethylene. The suture, provided in a #2 size, has the strength of #5 Ethibond, is ideally suited for most orthopedic procedures, and can be attached to a suture anchor or a curved needle.

The colored strands/sutures of the foregoing disclosures are intended to operate primarily for the health care provider's benefit. The prior art thus perceives a need for a suturing method whereby patients may be able to select a suture color for their particular wound as a means to improve or enhance the patient's mental or emotional reaction(s) to wound treatment and to shift focus away from the wound per se and more toward wound treatment via wound adornment as directed or aided through patient input and the availability of a wide range of suture colors. The present invention further contemplates variously color-demarcated banded sutures, whereby the bands can be used to help the user with proper suturing technique. As the prior art is silent on this type of suture construction, the present invention attempts to address this need.

SUMMARY OF THE INVENTION

The present invention thus attempts to structurally address the foregoing concerns and thus provides a method and kit for enabling patients to select colored sutures from a wide variety of colors. The colored sutures and suturing techniques together enable the patient to adorn a skin wound site as a means to more effectively treat the wound with the cooperation of the patient.

The present invention thus provides a suturing method and kit for adorning a suture site, which method essentially comprises the steps of: assessing a suture site or skin wound; selecting a suturing technique based on the assessed suture site or skin wound; and providing a visual depiction of exemplary suture layout schema to the patient, which exemplary suture layout schema are reflective of the selected suturing technique.

The patient may then be provided with a selection of suture colors or a suture color palette at or about which time the patient may be invited to select at least one suture color from the suture color palette. The patient may thus select at least one suture color from the selection of suture colors; and the suture site may be sutured with a colored suture as selected by the patent. It is contemplated that the suture kit may well comprise any number of variously colored sutures along with surgical needles to support the suturing method.

Each suture structure preferably comprises a suture length and a visually perceptible suture width. The suture length may preferably comprise a series of transverse suture bands, which bands extend intermediate superficial suture incisions for exposing the visually perceptible suture widths of successive suture bands in superficial adjacency to the skin adjacent the skin wound site. Notably, the entire suture width or visually perceptible diameter of each suture band comprises singular suture coloration, which singular suture coloration is reflective of the suture colors selected by the patient, but may differ from band to successive band.

Each of the sutures preferably further comprises a plurality of braided suture strands. As stated, the bands extend intermediate superficial suture incisions for exposing the visually perceptible suture widths of successive suture bands such that the entire suture width of each suture band comprises singular suture coloration extending across the plurality of braided suture strands. Thus, the singular suture coloration extending widthwise across the braided suture strands is reflective of the patient-selected suture colors for adorning the skin wound site.

In other words, differing suturing techniques and wound sites may require different suture-to-tissue bites. A selected suture structure, for example, may provide color-demarcated or color-banded sutures for guiding the suture installer during the suturing process. Exposed lengths of adjacent banded colors may well represent the proper suture-to-tissue bite widths. The lines of color demarcation may thus be roughly represented at minor incisions. The banded suture coloration may thus be said to provide certain suture-to-tissue bite width guide means for approximating proper suture-to-tissue bite width.

In an alternative suture construction according to the present invention, it is contemplated that the suture construction may alternatively comprise a suture length, a visually perceptible suture width, and a plurality of braided suture strands. The suture length may alternatively comprise a series of color-demarcated, transverse suture bands. The transverse suture bands may either comprise non-uniform, varied band widths, or uniform band widths.

In either structural configuration, the band widths sequentially sum to equal the suture length. The bands extend intermediate superficial suture incisions for exposing the visually perceptible suture widths of successive suture bands. It is contemplated that the varied band widths may well enable varied exposure lengths across the skin wound site, it being recognized that suturing practice often requires the physician to adorn a skin wound site with varied segments of the suture length (i.e. the band widths) across the skin wound site since skin wounds are often non-uniform in scope or dimension. Further, the entire suture width of each suture band width comprises singular suture coloration extending across the plurality of braided suture bands, which singular suture coloration is reflective of the selected suture colors for adorning the skin wound site.

A further feature of the varied, non-uniform band width is an epidermal marker, and dermal marker. The epidermis generally ranges in thickness from about 0.05 mm to about 2 mm, and the dermis generally ranges in thickness from about 1.5 mm to about 3.0 mm. It is contemplated that the epidermal markers 30 thus preferably comprise a band width on the order of between 0.05 and 2 mm, and the dermal markers may preferably comprise a band width on the order of between 4.5 and 10 mm (i.e. 3 lengths or sides X (1.5 mm-3.0 mm). The superficially exposed suture length or band widths may be of varying lengths depending on the type of suture technique employed, and may be cut and tied at the knot so that the exposed suture is of singular coloration.

It is thus contemplated that the band width(s) of the epidermal marker(s) may be inserted into the epidermal layer with the dermal marker being embedded within the dermal layer so that the suturing technician may properly apply the suturing technique. The exposed suture length of singular coloration may then be configured as needed to address/close the skin wound, while simultaneously adorning the site. In this regard, it is contemplated that the present suture construction may provide those learning proper suture techniques with visual cues for gauging proper suture depth and bite relative to the skin wound site.

BRIEF DESCRIPTION OF THE DRAWINGS

Other features of my invention will become more evident from a consideration of the following brief description of patent drawings:

FIG. 2(b) is a diagrammatic depiction of the second suturing technique for closing a skin wound showing the vertical mattress suture schematic with a third color pattern.

DETAILED DESCRIPTION OF THE PREFERRED EMBODIMENT/METHODOLOGY

Sutures or stitches may be classified into two main groups—those that are absorbable and those that are non-absorbable. Absorbable sutures or stitches are designed to break down harmlessly in the body over time without intervention. Non-absorbable sutures or stitches must be manually removed if they are not left indefinitely. The type of suture used varies on the operation, with the major criteria being the demands of the location and environment. The attending health care provider typically assesses the location and environment of the wound site and decides upon a preferred treatment method for suture-closing the wound site.

Sutures to be placed internally would require re-opening if they were to be removed. Sutures which lie on the exterior of the body can be removed within minutes, and without re-opening the wound. As a result, absorbable sutures are typically used internally whereas non-absorbable sutures are typically used externally. Exceptions to these general rules, however, are present. For example, sutures to be placed in a stressful environment, for example the heart, the bladder, or sternum may require specialized or stronger materials to perform their role. Typically, such sutures are either specially treated, or made of special materials, and are often non-absorbable to reduce the risk of degradation.

The present suture construction and attendant methodology concerns itself primarily with externally exposed sutures or stitches, which are readily viewable by the patient and passersby. The primary objective of the present invention is to involve the patient in the treatment process whereby the patient may be able to select a suture color and/or pattern more to their liking, and thereby shift focus away from the wound itself and more toward the treatment aspects. In other words, in a manner akin to a patient making a selection of cast color(s), it is contemplated that a patient-selected colored suture scheme may well improve the patient's cognitive approach to the treatment process.

Non-absorbable sutures are typically made of materials which are not metabolized by the body, and are used therefore either on skin wound closure, where the sutures can be removed after a few weeks, or in some inner tissues in which absorbable sutures are not adequate (e.g. heart and/or bladder). While there are several materials used for non-absorbable sutures, perhaps the most common non-absorbable sutures are made of artificial polymeric threadlike fibers such as polypropylene, polyester or nylon. For example, PROLENE sutures are polypropylene sutures that are most often provided with blue pigmentation and ETHILON sutures are nylon sutures that are most often provided with black pigmentation.

Figure 1:
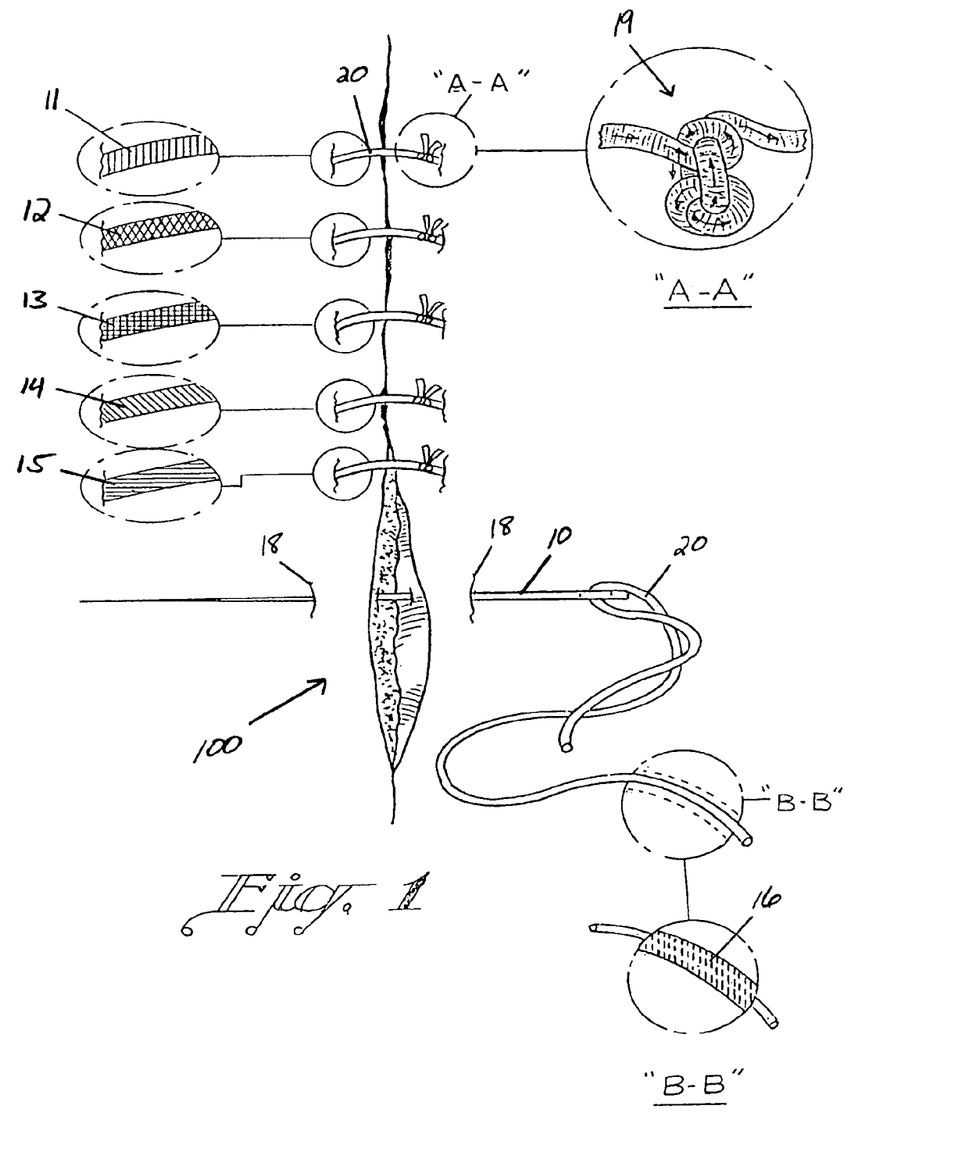
FIG. 1 is a diagrammatic depiction of a first suturing technique for closing a skin wound showing a simple interrupted suture schematic.
Figure 3:
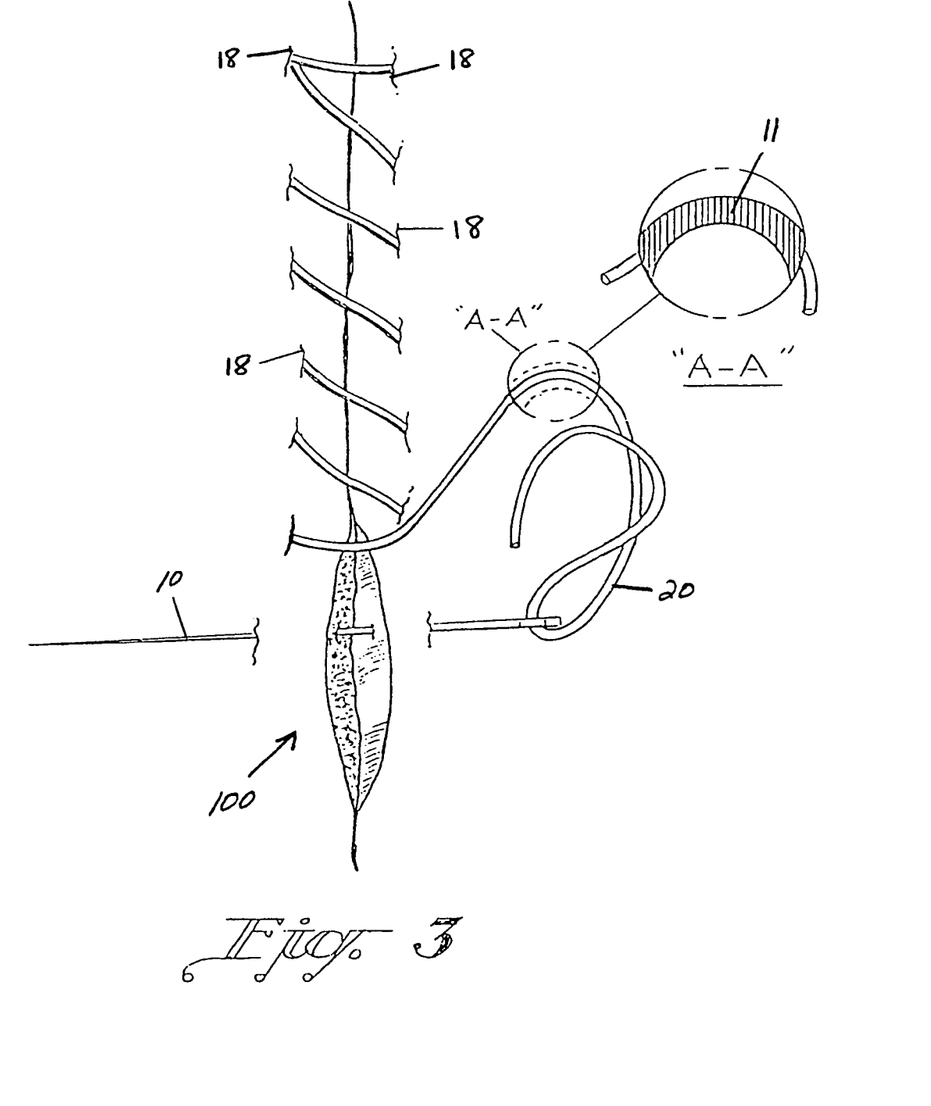
FIG. 3 is a diagrammatic depiction of a third suturing technique for closing a skin wound showing a continuous over-and-over suture schematic with a first color pattern.
Figure 3A:
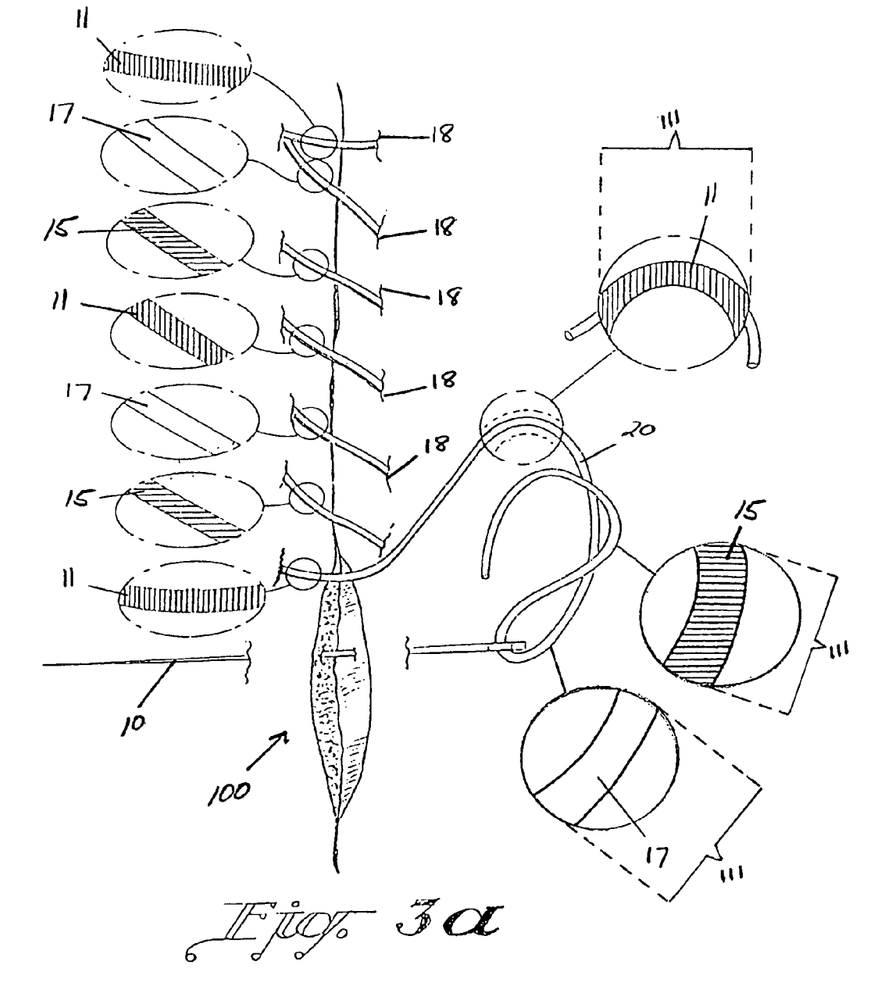
FIG. 3(a) is a diagrammatic depiction of the third suturing technique for closing a skin wound showing the continuous, running, or over-and-over suture schematic with a second color pattern.

Sutures are coupled to surgical needles prior to suturing a wound site. In this regard, there are two general classifications of surgical needles, namely, traumatic needles and atraumatic needles. Traumatic needles comprise holes or eyes through which the suture must be threaded on site. A traumatic needle 10 is illustrated in FIGS. 1, 3, and 3(a). It may be seen that the suture or thread comes out of the needle's hole or eye on both sides. When passing through tissue, this type of suture rips the tissue to a certain extent, thus prompting the descriptor: "traumatic".

Atraumatic needles with sutures comprise an eyeless needle attached to a specific length of suture thread. The suture manufacturer typically swages the suture thread to the eyeless atraumatic needle at the factory. There are several advantages to having the needle pre-mounted on the suture, including reduced suturing time (i.e. the health care provider does not have to spend time threading the suture on the needle) and the fact that with atraumatic sutures, the suture end of a swaged needle is smaller than the needle body thus minimizing tissue trauma. Nearly all modern sutures feature swaged atraumatic needles. Notably, atraumatic needles may be permanently swaged to the suture or may be designed to "pop-off" the suture with a sudden force. These so-called "pop-offs" are commonly used for interrupted sutures, where each suture is only passed once and then tied.

Suture gauges are defined by the United States Pharmacopeia (U.S.P.). Sutures were originally manufactured ranging in size from #1 to #6, with #1 being the thickest. A #4 suture might be roughly the diameter of a tennis racquet string. As manufacturing techniques improved, #0 was added to the suture diameters, and later, thinner and thinner threads were manufactured, which were identified as #00 (#2-0 or #2/0) to #000000 (#6-0 or #6/0).

Modern sutures range from #5 (i.e. a heavy braided suture typically utilized in orthopedic applications) to #11-0 (i.e. a fine monofilament suture typically utilized in ophthalmic applications). It is contemplated that the present invention incorporates the use of suture gauges having visually perceptible thicknesses or diameters so that the patient and/or passerby may be able to visually perceive the color and/or pattern scheme selected by the patient.

Referring now to the drawings with more specificity, the preferred methodology of the present invention concerns a skin wound treatment method for externally adorning a skin wound site (as generally referenced at 100) with suture(s) so as to improve the visual appearance of the wound site 100. The skin wound treatment method according to the present invention is contemplated to comprise the initial step of assessing a patient's skin wound site 100 by a trained or skilled health care provider.

In this regard, it is contemplated that the involvement of a trained health care provider is an important feature to the practiced methodology insofar as the wound site 100 must be addressed in a competent manner. The trained or skilled health care provider will select a suturing technique based upon the assessed skin wound site 100 and in this regard will propose at least one, but possibly a number of suturing techniques for suture-closing the wound site 100.

Figure 2:
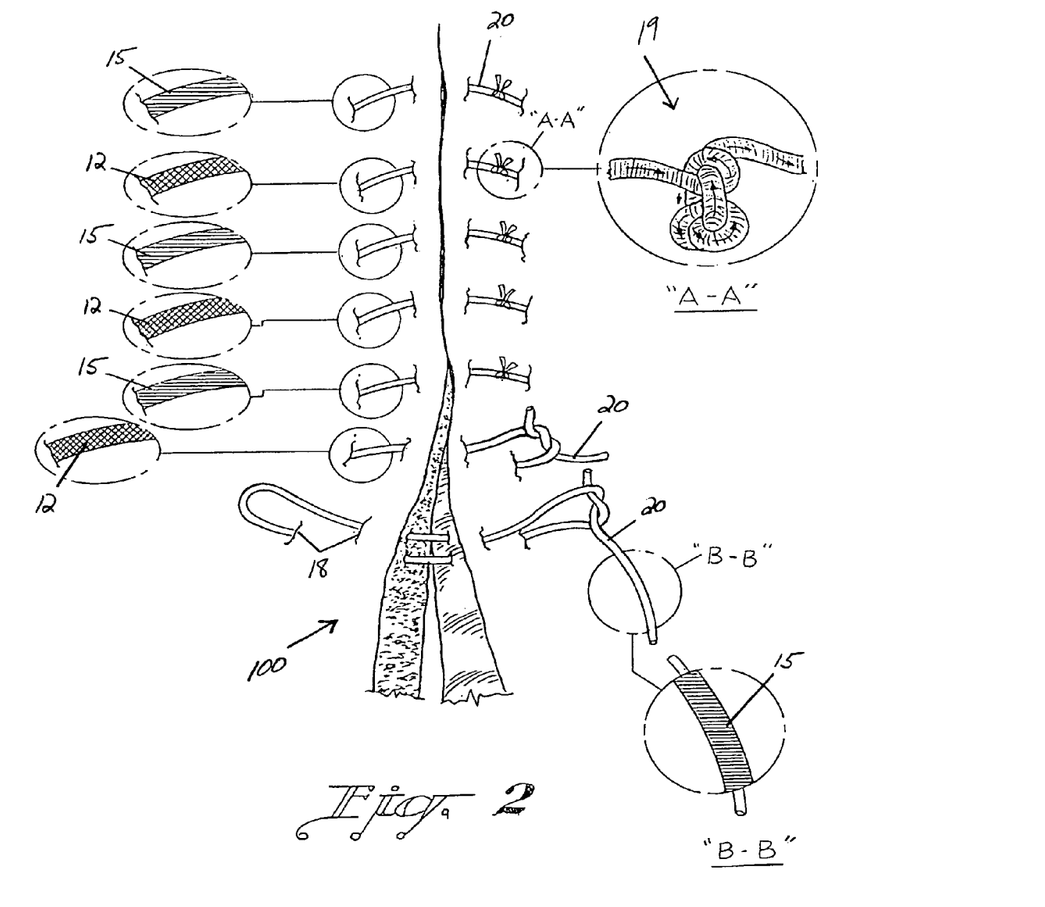
FIG. 2 is a diagrammatic depiction of a second suturing technique for closing a skin wound showing a vertical mattress suture schematic with a first color pattern.
Figure 4:
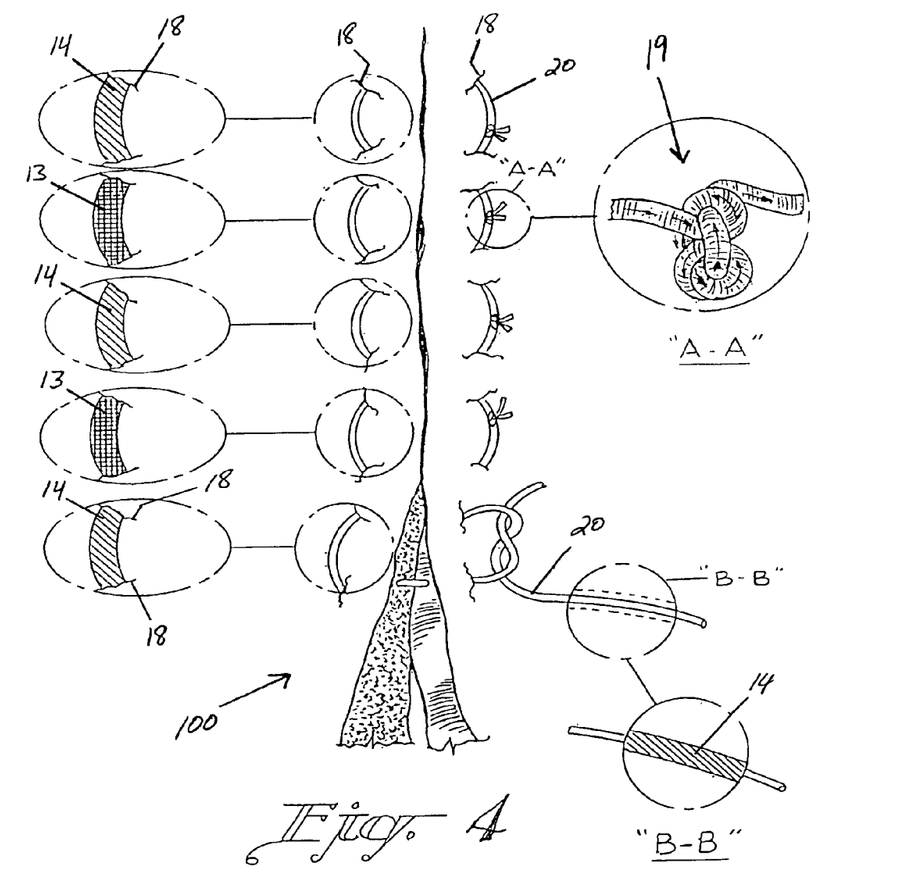
FIG. 4 is a diagrammatic depiction of a fourth suturing technique for closing a skin wound showing a horizontal mattress suture schematic with a first color pattern.

In this regard, it will be noted that FIG. 1 depicts a simple interrupted suture schematic; FIG. 2 shows a vertical mattress suture schematic; FIG. 3 shows a continuous, running, or over-and-over suture schematic; and FIG. 4 shows a horizontal mattress suture schematic. The illustrated suturing techniques are exemplary and not intended to be limiting. The chosen suturing technique selected by the health care provider will depend upon his or her training and practice sense for any given wound scenario.

Notably, proper suturing technique is essential to ensure good results in dermatologic surgery. The postoperative appearance of a beautifully designed closure or flap can be compromised if an incorrect suture technique is chosen or if the execution is poor. Conversely, meticulous suturing technique cannot fully compensate for improper surgical technique. Poor incision placement with respect to relaxed skin tension lines, excessive removal of tissue, or inadequate undermining may limit the surgeon's options in wound closure and suture placement.

Gentle handling of the tissue is also important to optimize wound healing. The choice of suture technique depends on the type and anatomic location of the wound, the thickness of the skin, the degree of tension, and the desired cosmetic result. The proper placement of sutures enhances the precise approximation of the wound edges, which helps minimize and redistribute skin tension.

Figure 5:
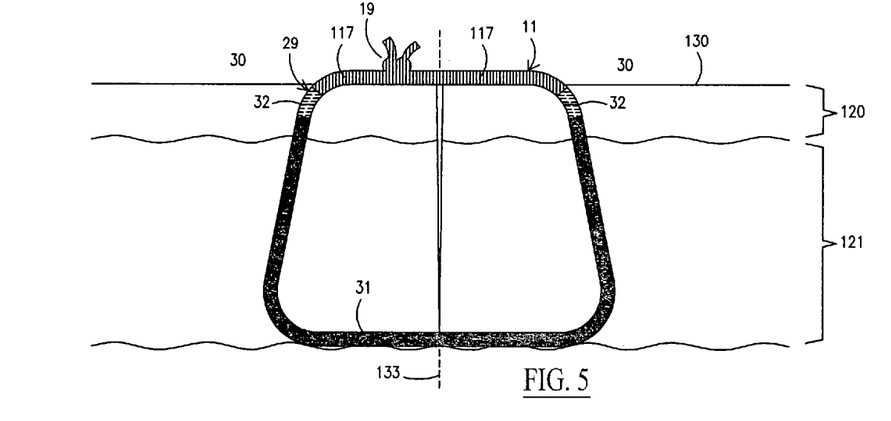
FIG. 5 is a diagrammatic depiction depicting a simple interrupted suture schematic in cross section through the skin layers to show various banded portions along the suture length relative to the skin structures/layers.
Figures 6, 6A:
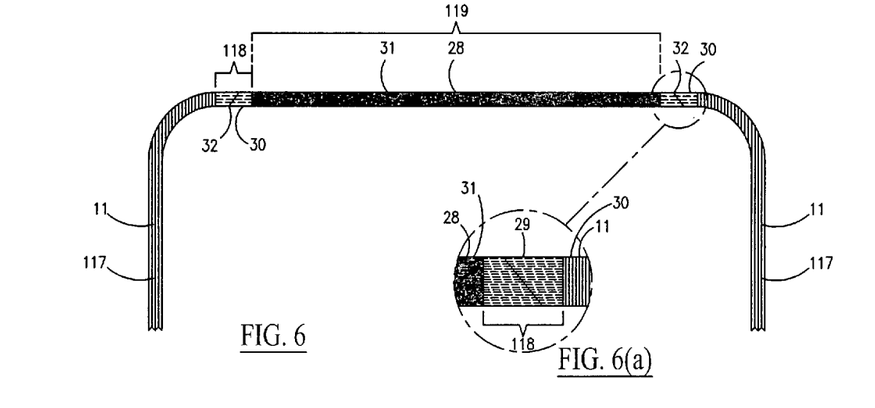
FIG. 6 is a diagrammatic depiction an enlarged, fragmentary length of suture otherwise depicted in FIG. 5, which length of suture comprises various color-demarcated, banded portions along the suture length.

The most commonly used and versatile suture in cutaneous surgery is the simple interrupted suture as generally depicted in FIGS. 1 and 5. This suture is placed by inserting the needle perpendicular to slightly angled relative to the epidermis, traversing the epidermis and the full thickness of the dermis, and exiting perpendicular to the epidermis on the opposite side of the wound. The two sides of the stitch should be symmetrically placed in terms of depth and width.

Compared with running sutures (as generally depicted in FIGS. 3 and 3(*a*)), interrupted sutures are typically easier to place, have greater tensile strength, and have less potential for causing wound edema and impaired cutaneous circulation. Interrupted sutures also allow the health care provider to make adjustments as needed to properly align wound edges as the wound is sutured. Disadvantages of interrupted sutures include the length of time required for their placement and the greater risk of crosshatched marks (i.e., train tracks) across the suture line. The risk of crosshatching can be minimized by removing sutures early to prevent the development of suture tracks.

The simple running suture or continuous over-and-over suture is generally illustrated in FIGS. 3 and 3(*a*). This type of suture technique employs an uninterrupted series of simple interrupted sutures. The suture is started by placing a simple interrupted stitch, which is tied but not cut. A series of simple sutures are placed in succession without tying or cutting the suture material after each pass. Sutures should be evenly spaced, and tension should be evenly distributed along the suture line. The line of stitches is completed by tying a knot (as generically depicted at 19) after the last pass at the end of the suture line. The knot is tied between the tail end of the suture material where it exits the wound and the loop of the last suture placed.

Running sutures are useful for long wounds in which wound tension has been minimized with properly placed deep sutures and in which approximation of the wound edges is good. This type of suture may also be used to secure a split- or full-thickness skin graft. Theoretically, less scarring occurs with running sutures compared with interrupted sutures because fewer knots are made with simple running sutures; however, the number of needle insertions remains the same.

Advantages of the simple running suture include quicker placement and more rapid re-approximation of wound edges, compared with simple interrupted sutures. Disadvantages include possible crosshatching, the risk of dehiscence if the suture material ruptures, difficulty in making fine adjustments along the suture line, and puckering of the suture line when the stitches are placed in thin skin.

The vertical mattress suture (as generally depicted in FIGS. 2-2(*c*)) is a variation of the simple interrupted suture. It consists of a simple interrupted stitch placed wide and deep into the wound edge and a second more superficial interrupted stitch placed closer to the wound edge and in the opposite direction. The width of the stitch should be increased in proportion to the amount of tension on the wound. That is, the higher the tension, the wider the stitch.

A vertical mattress suture is especially useful in maximizing wound eversion, reducing dead space, and minimizing tension across the wound. One of the disadvantages of this suture is crosshatching. The risk of crosshatching is greater because of increased tension across the wound and the four entry and exit points of the stitch in the skin. Placing each stitch precisely and taking symmetric bites is especially important with this suture.

The horizontal mattress suture (as generally depicted in FIG. 4) is placed by entering the skin 5 mm to 1 cm from the wound edge. The suture is passed deep in the dermis to the opposite side of the suture line and exits the skin equidistant from the wound edge (in effect, a deep simple interrupted stitch). The needle reenters the skin on the same side of the suture line 5 mm to 1 cm lateral of the exit point. The stitch is passed deep to the opposite side of the wound where it exits the skin and the knot is tied.

The horizontal mattress suture is useful for wounds under high tension because it provides strength and wound eversion. This suture may also be used as a stay stitch to temporarily approximate wound edges, allowing placement of simple interrupted or subcuticular stitches. The temporary stitches are removed after the tension is evenly distributed across the wound.

Horizontal mattress sutures may be left in place for a few days if wound tension persists after placement of the remaining stitches. In areas of extremely high tension at risk for dehiscence, horizontal mattress sutures may be left in place even after removal of the superficial skin sutures. However, they have a high risk of producing suture marks if left in place for longer than 7 days. Horizontal mattress sutures may be placed prior to a proposed excision as a skin expansion technique to reduce tension. Improved eversion may be achieved with this stitch in wounds without significant tension by using small bites and a fine suture.

In addition to the risk of suture marks, horizontal sutures have a high risk of tissue strangulation and wound edge necrosis if tied too tightly. Taking generous bites, using bolsters, and cinching the suture only as tightly as necessary to approximate the wound edges may decrease the risk, as does removing the sutures as early as possible. Placing sutures at a greater distance from the wound edge facilitates their removal.

It will thus be seen that suture technique and selection may be greatly benefited by input from a trained health care provider. Further, however, it will be seen that each technique provides a different visual presentation in superficial adjacency to the patient's skin at the wound site 100. For this reason it is contemplated that the present methodology may involve the step of providing a patient with a visual depiction of exemplary suture layout schema. Exemplary suture layout schemas are believed to be represented in FIGS. 1-4, inclusive. Notably, the suture layout schemas are reflective of the selected suturing technique.

Once the wound site has been assessed and a proper suturing technique decided upon, the patient may be provided with a suture color palette or selection of suture colors. In this last regard, it is contemplated that the suture color palette may well comprise any number of suture colors, including colors of varying electromagnetic wavelength ranging from about 400 nanometers (nm) to about 700 nanometers (nm), which wavelength range is roughly reflective of the visible color spectrum.

In this regard, FIG. 1 depicts a representative array or pattern of colored interrupted sutures, whereby red (700 nm) is referenced at 11; orange (600 nm) is referenced at 12; yellow (580 nm) is referenced at 13; green (530 nm) is referenced at 14; blue (480 nm) is referenced at 15; and purple or violet (400 nm) is referenced at 16. The resulting color patter red 11 (R), orange 12 (O), yellow 13 (Y), green 14 (G), blue 15 (B), and violet 16 (V), may be represented by ROY G BV as reflective of the famous mnemonic ROY G. BIV for the sequence of hues in the visible spectrum, in rainbows, and in order from longest to shortest electromagnetic wavelength. Other colors may include white 17, black 28, any shade of gray or silver 29, and any variation thereof.

The patient may thus select any color from the suture color palette or selection of suture colors and the skin wound site may then be sutured with at least one suture, each suture comprising suture coloration reflective of the selected suture color(s). For example, the patient may select any number of colors such as red 11, orange 12, yellow, 13, green 14, blue 15, and violet 16 and pattern or arrange these colors to represent the visible spectrum or rainbow as generally depicted in FIG. 1.

Figure 2A:
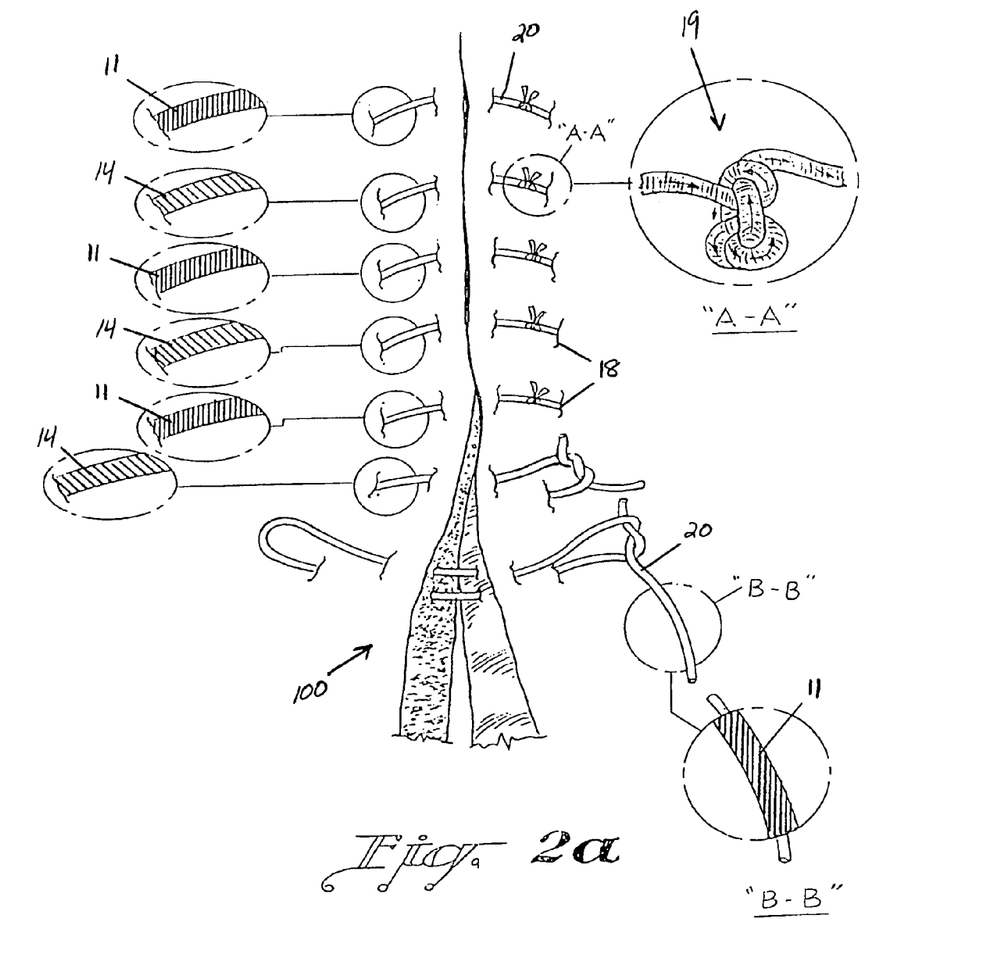
FIG. 2(a) is a diagrammatic depiction of the second suturing technique for closing a skin wound showing the vertical mattress suture schematic with a second color pattern.
Figure 2C:
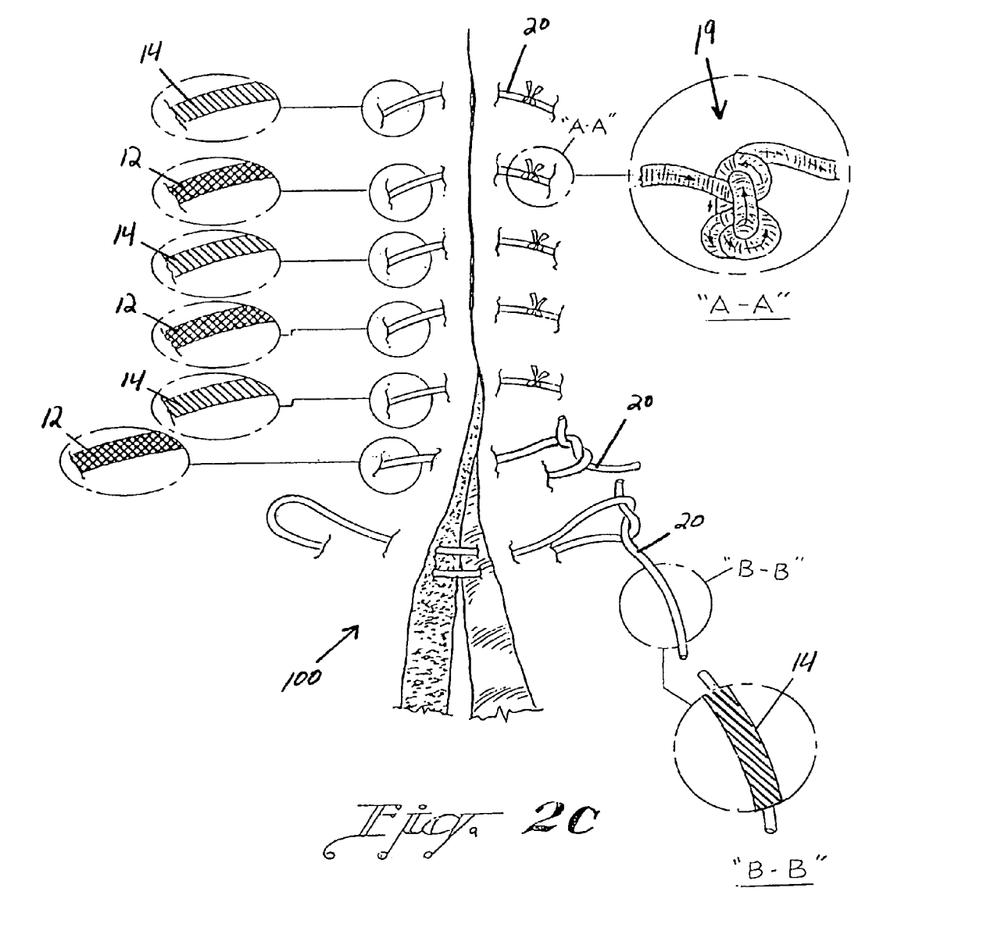
FIG. 2(c) is a diagrammatic depiction of the second suturing technique for closing a skin wound showing the vertical mattress suture schematic with a fourth color pattern.

Alternatively, the patient may select a color scheme (color and pattern) comprising alternating blue (15)—orange (12) colors to represent, for example, a favorite team color scheme as generally depicted in FIG. 2 or alternating green (14)—yellow (13) as generally depicted in FIG. 4. Further, the patient may select a color scheme comprising alternating red (11)—green (14) as generally depicted in FIG. 2(a); or red (11)—white (17) as generally depicted in FIG. 2(b); or green (14)—orange (12) to represent a holiday-themed color scheme (e.g. Christmas or Thanksgiving). FIG. 3(a) depicts a red (11)—white (17)—blue (15) color scheme generally representative of a 4$^{th}$ of July or Independence Day-type holiday theme.

In this last regard, it should be noted that the length of the suture 20 or suture structure may comprise various colors. In other words, each suture 20 may be multi-colored along its length. FIG. 3(a), for example, shows a continuous length of suture 20 having multiple colors (i.e. red (11), white (17), and blue (15)) along its length. It is contemplated that the demarcations between adjacent colors along the length of the suture 20 may well be spaced to help guide the health care provider for suture-tissue bites during the suturing process.

Each suture structure 20 preferably comprises a suture length and a visually perceptible suture width or diameter as at 110. The suture length may preferably comprise a series of transverse suture bands as at 111, which bands 111 extend intermediate superficial suture incisions 18 for exposing the visually perceptible suture widths 110 of successive suture bands 111 in superficial adjacency to the skin adjacent the skin wound site 100. Notably, the entire suture width or visually perceptible diameter 110 of each suture band 111 comprises singular suture coloration, which singular suture coloration is reflective of the suture colors selected by the patient, but may differ from band 111 to successive band 111 as generally and comparatively depicted in FIGS. 3(a) and 4.

Figures 7, 7A, 7B, 7C, 7D:
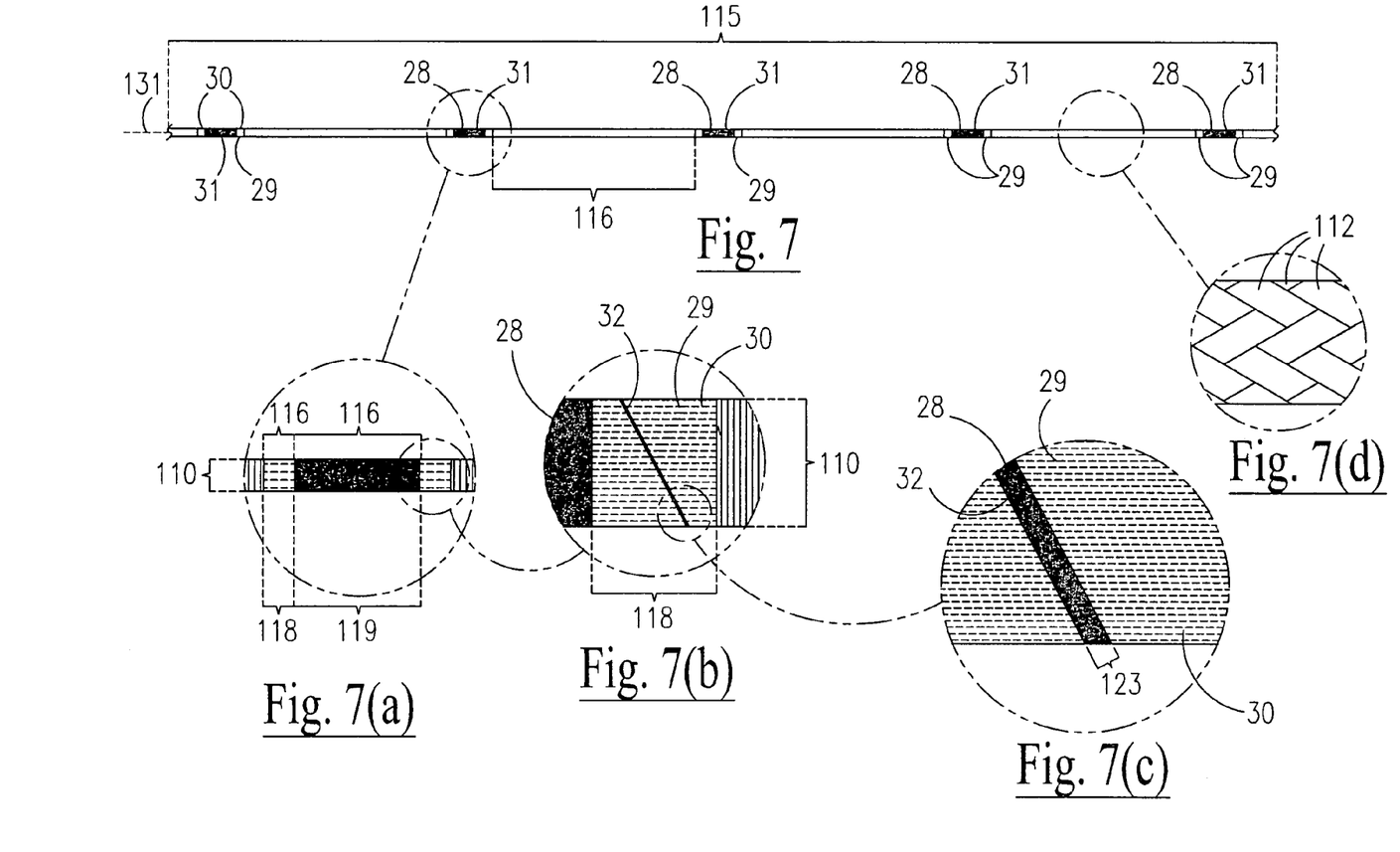
FIG. 7 is a reduced, fragmentary length of suture to show variously patterned, color-demarcated banded portions along the suture length.
FIG. 7(a) is an enlarged, fragmentary sectional view of a banded portion otherwise depicted in FIG. 7 to show greater detail thereof.
FIG. 7(b) is an enlarged, fragmentary sectional view of the banded portion otherwise shown in FIG. 7(a) to show greater detail thereof.
FIG. 7(c) is an enlarged, fragmentary sectional view of the banded portion otherwise shown in FIG. 7(b) to show greater detail thereof.
FIG. 7(d) is an enlarged view of the suture construction showing a braided multi-strand configuration.

In this last regard, the reader should further note that each of the sutures 20 preferably further comprise a plurality of strands as generally depicted and referenced at 112 in FIGS. 7(b) and 7(c). As stated, the bands 111 extend intermediate superficial suture incisions 18 for exposing the visually perceptible suture widths 110 of successive suture bands 111 such that the entire suture width 110 of each suture band 111 comprises singular suture coloration extending across the plurality of braided suture strands 112. Thus, the singular suture coloration extending widthwise across the strands 112 is reflective of the patient-selected suture colors for adorning the skin wound site 100.

In other words, differing suturing techniques and wound sites may require different suture-to-tissue bites. A selected suture structure 20, for example, may provide color-demarcated or color-banded sutures for guiding the suture installer during the suturing process. Exposed lengths of adjacent banded colors may well represent the proper suture-to-tissue bite widths. The lines of color demarcation may thus be roughly represented at minor incisions 18. The banded suture coloration may thus be said to provide certain suture-to-tissue bite width guide means for approximating proper suture-to-tissue bite width.

In an alternative suture construction according to the present invention, it is contemplated that the suture construction may alternatively comprise a suture length as at 115, a visually perceptible suture width as at 110, and a plurality of braided suture strands 112. The suture length 115 may alternatively comprise a series of color-demarcated, transverse suture bands as at 111. The transverse suture bands 111 may either comprise non-uniform, varied band widths 116 as generally depicted in FIGS. 5-7(b) or uniform band widths 117 as generally depicted in FIG. 3(a).

In either structural configuration, the band widths 116 or 117 sequentially sum to equal the suture length 115. The bands 111 extend intermediate superficial suture incisions 18 for exposing the visually perceptible suture widths 110 of successive suture bands 111. It is contemplated that the varied band widths 116 may well enable varied exposure lengths across the skin wound site 100, it being recognized that suturing practice often requires the physician to adorn a skin wound site 100 with varied segments of the suture length (i.e. the band widths) across the skin wound site 100 since skin wounds are often non-uniform in scope or dimension. Further, the entire suture width 110 of each suture band width 116 comprises singular suture coloration extending across the plurality of braided suture bands 112, which singular suture coloration is reflective of the selected suture colors for adorning the skin wound site 100.

A further feature of the varied, non-uniform band width is generally depicted in FIGS. 5-7(c). From a comparative inspection of the noted figures, it will be seen that the suture construction 20 may further comprise epidermal markers as at 30 and dermal markers as at 31. The epidermis generally ranges in thickness from about 0.05 mm to about 2 mm as referenced at 120, and the dermis generally ranges in thickness from about 1.5 mm to about 3.0 mm as referenced at 121. It is contemplated that the epidermal markers 30 thus preferably comprise a band width on the order of between 0.05 and 2 mm as at 118, and the dermal markers may preferably comprise a band width on the order of between 4.5 and 10 mm as at 119. The superficially exposed suture length or band widths as at 117 may be of varying lengths depending on the type of suture technique employed, and may be cut and tied at the knot 19 so that the exposed suture is of singular coloration.

If the skin wound site 100 calls for a simple interrupted suturing technique, then the band widths 117 may be something on the order of 10 to 20 mm. If a continuous over-and-over suture technique is called for, then the band widths 117 may be something on the order of 10-50 mm. The superficial or exposed suture lengths or band widths may be tailored, and the figures set forth here are exemplary. More fixed are the epidermal and dermal market band widths 118 and 119 respectively insofar as the typical epidermal layer thickness 120 and dermal layer thickness 121 are more or less consistent, whereas the exposed band widths 117 may be subject to more tailored length according to the needs of the patient/physician.

It is thus contemplated that the band width 118 of the epidermal marker(s) 30 may be inserted into the epidermal layer 120 with the dermal marker 31 being embedded within the dermal layer 121 so that the suturing technician may properly apply the suturing technique. The exposed suture length of singular coloration may then be configured as needed to address/close the skin wound, while simultaneously adorning the site 100. In this regard, it is contemplated that the present suture construction may provide those learning proper suture techniques with visual cues for gauging proper suture depth and bite relative to the skin wound site 100.

A further feature according to the present invention is the inclusion of a marker angle indicator as at 32. While some suturing techniques call for suture insertion orthogonal to the plane of the skin, other suture techniques call for a slight oblique insertion relative to the plane of the skin so that proper bite and closure can occur via the suture technique employed. The present invention thus contemplates the placement of a marker angle indicator 32 for providing a visual cue to the technician.

Referencing FIG. 5, it will be seen that after insertion, the marker angle indicators 32 are roughly parallel to the plane of the skin surface as at 130, but obliquely angled relative to the axis 131 of the suture length. Depending on the angle of the indicator 32, the technician should aim to align the marker angle indicator 32 with a fixed plane of reference either in parallel or in orthogonal relationship thereto. The marker angle indicator 32 preferably comprises a visually perceptible width as at 123 with a color contrast relative to the band in which it is located.

Conceivably, the proper placement of the indicator 32 is within the epidermal markers 30 substantially as shown, such that a black indicator 32 may be found within a silver epidermal marker 30. Given that the entrance angle and the exit angle are ideally congruous about the plane 133 of the skit wound site 100, it is further contemplated that the marker angle indicators surrounding a given dermal marker 31 are oppositely angled relative to one another such that when inserted into a skin wound site, the indicators will both be substantially equally aligned relative to the fixed plane of reference. The markers 30 and 31 optionally outfitted with indicators 32 may thus also exemplify certain suture-to-tissue bite width guide means according to the present invention.

While the foregoing specifications and attached drawings are set forth in some detail, the specific procedures and supporting embodiments described and illustrated are to be considered as exemplifications of the principles of the invention and are not intended to limit the invention(s) to the specific methods and/or embodiments illustrated or described. For example, it is contemplated that the present invention essentially discloses a skin wound treatment method or suturing method.

The skin wound treatment method or suturing method according to the present method is essentially set forth for externally adorning a skin wound site or suture site. The skin wound treatment method may be said to comprise the steps of: assessing a patient's skin wound site, which site is assessed by a medical or health care provider. A suturing technique is then selected as based upon the assessed skin wound site. When a suturing technique is decided upon, the patient may be provided with visual depiction(s) of exemplary suture layout schema, which schema are reflective of the selected suturing technique. The patient may thus obtain a visual depiction of how his or her suture, when completed with structurally appear.

When the patient has an understanding for how the suture 20 will appear adjacent the wound site, he or she will have a better opportunity to select any number of suture colors as provided the patient via a suture color palette or selection of suture colors. Further, the patient then has an opportunity to arrange or pattern the colors according to his or her selections and the preferred suture technique. The skin wound site may then be sutured with one or more lengths of suture 20, each of which comprises suture coloration reflective of the patient-selected suture color(s).

Stated another way, the suturing method according to the present invention may be said to essentially comprise the steps of: providing a patient with a selection of suture colors; inviting the patient to select at least one suture color from the suture color palette; selecting at least one suture color from the selection of suture colors; and suturing a suture site with a suture, the suture comprising the selected suture color. The method may be said to comprise the additional steps of assessing the suture site; selecting a suturing technique based on the assessed suture site; and providing a visual depiction of exemplary suture layout schema to the patient, the exemplary suture layout schema being reflective of the selected suturing technique.

The selection of suture colors may comprise any color, including colors of varying electromagnetic wavelengths ranging from about 400 nm to about 700 nm. The sutures may further comprise a suture length, which length may comprise colors of varying electromagnetic wavelengths along the entire visible spectrum. The colors may be spaced along the length of the suture length to serve as bite length guide way demarcations for the suture(s) 20.

The suturing method may be supported by a suture kit comprising any number of suture colors and styles according to the presenting methodology and supporting embodiment(s), along with suture needles of any type and style. Preferably, however, it is contemplated that the kit may include or comprise sutures either permanently or temporarily swaged to needles.

From the foregoing, it will be observed that numerous variations and modifications of the disclosed methodology and underlying suture structure 20 may be effected without departing from the spirit and scope of the invention. Thus, it is to be understood that no limitation with respect to the specific structure(s) and/or methodology illustrated herein is intended or should be inferred. It is, of course, intended to cover by the appended claims all such modifications as fall within the scope of the claims.

I claim:

1. A skin wound treatment method, the skin wound treatment method for externally adorning a skin wound site, the skin wound treatment method comprising the steps of:
    assessing a patient's skin wound site, the patient's skin wound site being assessed by a health care provider;
    selecting a suturing technique based on the assessed skin wound site, the suturing technique being selected by the health care provider;
    providing a patient with a visual depiction of exemplary suture layout schema, the suture layout schema being reflective of the selected suturing technique;
    providing the patient with a suture color palette, the suture color palette comprising a plurality of suture colors;
    selecting at least two suture colors from the suture color palette, each suture color being selected by the patient; and
    suturing the skin wound site with at least one suture construction, each suture construction comprising a suture length, a visually perceptible suture width, epidermal markers and a dermal marker, the suture length comprising a series of color-demarcated, transverse suture bands, the suture bands comprising non-uniform, varied band widths, the band widths sequentially summing to equal the suture length, the suture bands for extending intermediate superficial suture incisions for exposing the visually perceptible suture widths of successive suture bands, the varied band widths for enabling varied exposure lengths across the skin wound site, and some suture bands defining the epidermal and dermal markers, the epidermal markers flanking the dermal marker for aiding the user in proper suture technique during suture application, the entire suture width of each suture band width comprising singular suture coloration, the singular suture coloration being reflective of the selected suture colors for adorning the skin wound site, a select marker selected from the group consisting of the epidermal markers and the dermal marker comprising at least one marker angle indicator, the at least one marker angle indicator being obliquely angled relative to a suture length axis of the suture length and configured for roughly parallel positioned placement relative to a skin surface during suture application, the at least one marker angle indicator being color-contrasted relative to a suture band in which it is located and for aiding the user in proper suture technique during suture application.

2. The method of claim 1 comprising at least two opposed marker angle indicators, the two opposed marker angle indicators being cooperably associated with the epidermal markers flanking the dermal marker, the two marker angle indicators being oppositely angled relative to the suture length axis for roughly parallel positioned placement to the skin surface during suture application.

3. The method of claim 2 wherein the epidermal markers comprise epidermal marker band widths between 0.05 mm and 2 mm and the dermal marker comprises a dermal marker band width between 4.5 mm and 10 mm, the epidermal and dermal marker band widths for providing the user with visual cues as to proper suture depth and bite during suture application.

4. The method of claim 2 wherein the marker angle indicators comprise a visually perceptible width, the visually perceptible widths each comprising contrasting color relative to the epidermal markers for aiding the user in proper suture technique during suture application.

5. The method of claim 1 wherein the suture color palette comprises colors of varying electromagnetic wavelengths, the varying electromagnetic wavelengths ranging from about 400 nm to about 700 nm.

6. The method of claim 1 wherein the selected suture colors are patterned, the selected suture colors being patterned according to the patient's instructions before suturing the skin wound site with the plurality of sutures.

7. The method of claim 1 comprising the steps of: selecting at least three suture colors from the suture color palette, each suture color being selected by the patient; and suturing the skin wound site with a plurality of sutures, each suture comprising select suture coloration, the selected suture coloration being reflective of the selected suture colors.

8. A suture construction for suture-adorning a suture site, the suture construction comprising:
    a suture length, a visually perceptible suture width, epidermal markers and a dermal marker, the suture length comprising a series of color-demarcated, transverse suture bands, the suture bands comprising non-uniform, varied band widths, the band widths sequentially summing to equal the suture length, the suture bands for extending intermediate superficial suture incisions for exposing the visually perceptible suture widths of successive suture bands, the varied band widths for enabling varied exposure lengths across the skin wound site, and some suture bands defining the epidermal and dermal markers, the epidermal markers flanking the dermal marker for aiding the user in proper suture technique during suture application, the entire suture width of each suture band width comprising the selected singular suture color, a select marker selected from the group consisting of the epidermal markers and the dermal marker comprising at least one marker angle indicator, the at least one marker angle indicator being obliquely angled relative to a suture length axis of the suture length and configured for roughly parallel positioned placement relative to a skin surface during suture application, the at least one marker angle indicator being color-contrasted relative to a suture band in which it is located and for aiding the user in proper suture technique during suture application.

9. The suture construction of claim 8 comprising at least two opposed marker angle indicators, the two opposed marker angle indicators being cooperably associated with the epidermal markers flanking the dermal marker, the two marker angle indicators being oppositely angled relative to the suture length axis for roughly parallel positioned placement to the skin surface during suture application.

10. The suture construction of claim 9 wherein the epidermal markers comprise epidermal marker band widths between 0.05 mm and 2 mm and the dermal marker comprises a dermal marker band width between 4.5 mm and 10 mm, the epidermal and dermal marker band widths for providing the user with visual cues as to proper suture depth and bite during suture application.

11. The suture construction of claim 9 wherein the marker angle indicators comprise a visually perceptible width, the visually perceptible widths each comprising contrasting color relative to the epidermal markers for aiding the user in proper suture technique during suture application.

12. The suture construction of claim 8 wherein the selection of suture colors comprises colors of varying electromagnetic wavelengths, the varying electromagnetic wavelengths ranging from about 400 nm to about 700 nm.

13. The suture construction of claim 8 wherein the selected suture colors are patterned according to the patient's instructions before suturing the suture site.

14. A suture kit, the suture kit for enabling a suture provider to adorn a suture site with patient-selected colored sutures, the suture kit comprising: a plurality of sutures, each suture comprising a suture length, a visually perceptible suture width, epidermal markers and a dermal marker, the suture length comprising a series of color-demarcated, transverse suture bands, the suture bands comprising non-uniform, varied band widths, the band widths sequentially summing to equal the suture length, the suture bands for extending intermediate superficial suture incisions for exposing the visually perceptible suture widths of successive suture bands, the varied band widths for enabling varied exposure lengths across the skin wound site, and some suture bands defining the epidermal and dermal markers, the epidermal markers flanking the dermal marker for aiding the user in proper suture technique during suture application, the entire suture width of each suture band width comprising selected singular suture color for adoring the suture site, the suture coloration comprising varying electromagnetic wavelengths, the varying electromagnetic wavelengths ranging from about 400 nm to about 700 nm, a select marker selected from the group consisting of the epidermal markers and the dermal marker comprising at least one marker angle indicator, the at least one marker angle indicator being obliquely angled relative to a suture length axis of the suture length and configured for roughly parallel positioned placement relative to a skin surface during suture application, the at least one marker angle indicator being color-contrasted relative to a suture band in which it is located and for aiding the user in proper suture technique during suture application.

15. The suture kit of claim 14 wherein each suture construction comprises at least two opposed marker angle indicators, the two opposed marker angle indicators being cooperably associated with the epidermal markers flanking the dermal marker, the two marker angle indicators being oppositely angled relative to the suture length axis for roughly parallel positioned placement to the skin surface during suture application.

16. The suture kit of claim 15 wherein the epidermal markers comprise epidermal markers comprise epidermal marker band widths between 0.05 mm and 2 mm and the dermal marker comprises a dermal marker band width between 4.5 mm and 10 mm, the epidermal and dermal marker band widths for providing the user with visual cues as to proper suture depth and bite during suture application.

17. The suture kit of claim 15 wherein the marker angle indicators comprise a visually perceptible width, the visually perceptible widths each comprising contrasting color relative to the epidermal markers.

18. The suture kit of claim 14 comprising at least one surgical needle.

19. The suture kit of claim 18 wherein the surgical needle is swaged to a select suture.

* * * * *